United States Patent
Park

(10) Patent No.: US 9,884,041 B2
(45) Date of Patent: Feb. 6, 2018

(54) COMPOSITION FOR THE PREVENTION OR TREATMENT OF OBESITY, DYSLIPIDAEMIA, FATTY LIVER OR INSULIN RESISTANCE SYNDROME, COMPRISING PIPERONAL AS AN ACTIVE INGREDIENT

(75) Inventor: Tae Sun Park, Seoul (KR)

(73) Assignee: YONSEI UNIVERSITY TECHNOLOGY HOLDINGS, INC., Incheon (KR)

(*) Notice: Subject to any disclaimer, the term of this patent is extended or adjusted under 35 U.S.C. 154(b) by 537 days.

(21) Appl. No.: 13/695,651

(22) PCT Filed: Nov. 19, 2010

(86) PCT No.: PCT/KR2010/008206
§ 371 (c)(1),
(2), (4) Date: Nov. 1, 2012

(87) PCT Pub. No.: WO2011/139010
PCT Pub. Date: Nov. 10, 2011

(65) Prior Publication Data
US 2013/0116315 A1  May 9, 2013

(30) Foreign Application Priority Data
May 3, 2010 (KR) ......................... 10-2010-0041249

(51) Int. Cl.
*A61K 31/36* (2006.01)
*A23L 33/105* (2016.01)

(52) U.S. Cl.
CPC ............ *A61K 31/36* (2013.01); *A23L 33/105* (2016.08); *A23V 2200/00* (2013.01)

(58) Field of Classification Search
USPC ....................................................... 514/464
See application file for complete search history.

(56) References Cited

U.S. PATENT DOCUMENTS

2008/0044487 A1* 2/2008 Bruheim et al. .............. 424/522

FOREIGN PATENT DOCUMENTS

EP 0 997 137 B1 6/2002
WO WO2007101349 A1 * 9/2007

OTHER PUBLICATIONS

Ang et al. (1999) Asian Foods Science and Technology pp. 429.*
Das. Is Obesity an Inflammatory Condition?. Nutrition (2001), vol. 17, pp. 953-966.*
Handbook of Indices of Food Quality and Authenticity (1997) chapter 3, pp. 112.*
Bjørsvik et al. Organic Process Research and Development (2000), vol. 4, pp. 534-543.*
International Search Report from International Application No. PCT/KR2010/008206, dated Jul. 28, 2011 (date of completion of search) and dated Jul. 29, 2011 (date of mailing of report).

* cited by examiner

*Primary Examiner* — Kendra D Carter
*Assistant Examiner* — Taina D Matos Negron
(74) *Attorney, Agent, or Firm* — Clark & Elbing LLP; Susan M. Michaud

(57) ABSTRACT

Provided is a composition for the prevention or treatment of obesity, dyslipidaemia, fatty liver or insulin resistance syndrome, comprising piperonal as an active ingredient. The composition of the present invention can be used to advantage as a drug or functional food composition which not only exhibits activity in the prevention or treatment of obesity, hyperlipidaemia or fatty liver but which also causes a significant reduction in fasted blood sugar and blood insulin concentration and hence has an effect in improving Type-2 diabetes or insulin resistance and also improves metabolic disorder which is closely associated therewith.

10 Claims, 12 Drawing Sheets

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gggacctaca atgcttacag                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ggtcatatgt caccagctct                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
acggatgtgg tgaaggtccg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tacaaacatc atcacgttcc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
agaacatcat ccctgcatcc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tccaccaccc tgttgctgta                                              20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 7
ttcggaatca gctctgtgga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ccattgggtc agctcttgtg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
agcatcataa ccctagatgg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gaagtcacgc ctttcataac                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tcggtgcgtc taagatgagg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
tcaaggcaca tttttgctcc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
tgtctcagcc tcttctcatt                                              20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
agatgatctg agtgtgaggg                                                   20

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
atgaagttcc tctctgcaag agact                                             25

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
cactaggttt gccgagtaga tctc                                              24
```

COMPOSITION FOR THE PREVENTION OR TREATMENT OF OBESITY, DYSLIPIDAEMIA, FATTY LIVER OR INSULIN RESISTANCE SYNDROME, COMPRISING PIPERONAL AS AN ACTIVE INGREDIENT

CROSS-REFERENCE TO RELATED APPLICATIONS

This application is the U.S. national stage filing under 35 U.S.C. §371 of international application PCT/KR2010/008206, filed Nov. 19, 2010, which claims priority from Korea Patent Application 10-2010-0041249, filed May 3, 2010.

BACKGROUND OF THE INVENTION

Field of the Invention

The present invention relates to a composition for preventing or treating obesity, dyslipidemia, fatty liver or insulin resistance syndrome containing piperonal as an active ingredient.

Background of Technique

As abdominal obesity increases in modern people with the change in lifestyles, occurrence of metabolic syndromes including diabetes, hypertension, dyslipidemia, insulin resistance, etc. is increasing rapidly. These diseases increase the risk of incidence one another and are commonly related to the cause of metabolic changes, such as aging, stress and suppressed immune system. Obesity is considered unattractive and causes such chronic diseases as fatty liver, hypertension, diabetes, cardiovascular diseases, or the like. According to the 2007 Korea National Health and Nutrition Examination Survey recently reported by the Ministry of Health & Welfare, 31.7% of Korean adults turned out to be obese, meaning that 3 out of 10 Korean adults are exposed to obesity-related complications. The increase in overweight and obese population leads to increased prevalence of chronic diseases. The number of diabetic patients in Korea is expected to increase from 3,000,000 in 2007 to 5,450,000 in 2030, meaning that 10% of Koreans will be diabetic patients. In 2005, deaths caused by diabetes in Korea were 35.5 per 100,000 people, 3-7 times more than those of Japan (5.9), England (7.5) or Germany (16.6). According to the Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in adults and to 15% in youth, and is exploring ways to accurately define and diagnose obesity and metabolic diseases.

At present, 1.7 billion people amounting to about 25% of the world population are overweight (BMI>25) and more than 300 million people including 120 million in the US, Europe and Japan are classified as obese (BMI>30). Among the OECD countries, the US has the highest obesity rate of 31% of population, followed by Mexico (24%), England (23%), Greece (22%), Australia (22%), New Zeeland (21%), Hungary (19%), Canada (14%), Spain (13%), Ireland (13%), Germany (13%), Portugal (13%), Finland (13%), Turkey (12%) and Belgium (12%). The number of obese people in China is 70 million and the body weight control-related market is expanding, estimated at about 10 billion yuan. Childhood obesity is also increasing rapidly worldwide, with 1 in 5 children being obese. As such, childhood obesity is becoming a serious social issue. Since childhood obesity is the main cause of the life style diseases including diabetes, hypertension, stroke, etc. with increased blood cholesterol and triglyceride level, 80% or more of obese children are likely to become obese adults. Further, since increased fat stimulates secretion of sex hormones and induces early adolescence, childhood obesity may cause growth problems. Also, it negatively affects blood circulation and nourishment.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related side effects such as steatorrhea, gas generation and reduced absorption of oil-soluble vitamins. Reductil, which increases serotonin and noradrenaline levels in the sympathetic nervous system, has side effects such as headache, dry mouth, loss of appetite, insomnia, constipation, etc. Besides, a large number of anti-obesity drugs have been withdrawn from the market due to severe side effects. For example, aminophylline is reported to have various side effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in side effects and in overcoming chronic diseases, foods and drugs derived from natural sources are drawing attentions.

Piperonal is named as heliotropine (heliotropin), dioxymethyleneprotocatechuic aldehyde, piperonyl aldehyde, 3,4-benzodioxole-5-carboxaldehyde, 1,3-benzodioxole-5-carboxaldehyde, 3,4-methylene dihydroxybenzaldehyde. Piperonal contained in *Capparis spinosa* Linne (Caper), *Cinnamomum camphora* (Camphor), *Cucumis melo* Linn, *Galium verum* var. *asiaticum*, *Piper nigrum* (Black Pepper), *Polianthes tuberosa* (Tuberose), *Vaccinium colymbosum* (American blueberry), *Vanilla planifolia* (Bourbon vanilla), *Viola odorata* (Apple leaf) is alkaloids compounds.

Piperonal has the molecular formula of $C_8H_6O_3$ and the molecular weight of 150.13 g/mol, represented by the following chemical formula:

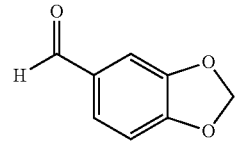

Piperonal has been registered in the food additives database of FDA (Food and Drug Administration) and KFDA (Korea Food and Drug Administration) as flavoring substance with edible substance. It has been also used for combination of spices based on cherry and vanilla, and ice cream and bakery products mainly. Piperonal has been reported to have cancer inhibitory effect in cancinogenesis animal model (Anto R J, George J, Babu K V, Rajasekharan K N, Kuttan R., Antimutagenic and anticarcinogenic activity of natural and synthetic curcuminoids. *Mutat Res*. September 13; 370(2):127-31 (1996)). It has been also reported that patients feel relief from anxiety as a result of stimulated sense of smell by piperonal through nasal cannula during MRI (magnetic resonance imaging) for cancer diagnosis (Redd W H, Manne S L, Peters B, Jacobsen P B, Schmidt H., Fragrance administration to reduce anxiety during MR imaging. *J Magn Reson Imaging*. July-August; 4(4):623-6, 1994).

Piperonal is known as an edible substance with a significant high safety. In other words, there was no toxicity although human took 10 g of piperonal (Von Oettingen, W. F., Nat *Inst Health Bull*. No. 190, 342 (1949)) and it is noteworthy that the reported $LD_{50}$ of piperonal is more than 2,700 mg/kg (rats) (Jenner, P. M., et al., *Food Cosmet Toxicol*. 2, 327, (1964)). Furthermore, there were no abnormalities on blood, weight of major organs and histology in an experiment of intaking feed containing 1% piperonal to rats for 28 weeks (Hagan, E. C., et al., *Fd Cosmet Toxicol*. 5, 141 (1967)). There was no toxicity in an experiment of intaking feed containing 0.1% piperonal and 0.5% piperonal to rats for 2 years (FAO Nutr. Meet. Rep. Ser. No. 44A. WHO Fd. Add. 68, 33, 73, (1968)).

Throughout the specification, a number of publications and patent documents are referred to and cited. The disclosure of the cited publications and patent documents is incorporated herein by reference in its entirety to more clearly describe the state of the related art and the present disclosure.

SUMMARY OF THE INVENTION

The present inventors have made intensive studies to develop natural substance or compounds derived from natural substance having prevention or therapeutic efficacies for metabolic diseases including obesity, dyslipidemia and/or fatty liver. As a result, they have found out that piperonal is significantly effective in improvement of the lipid metabolic diseases.

Accordingly, it is an object of this invention to provide a composition for preventing or treating obesity, dyslipidemia, fatty liver or insulin resistance syndrome.

It is another object of this invention to provide a method for preventing or treating obesity, dyslipidemia, fatty liver or insulin resistance syndrome.

Other features and aspects will be apparent from the following detailed description, drawings and claims.

DETAILED DESCRIPTION OF THE INVENTION

Figure 1A:
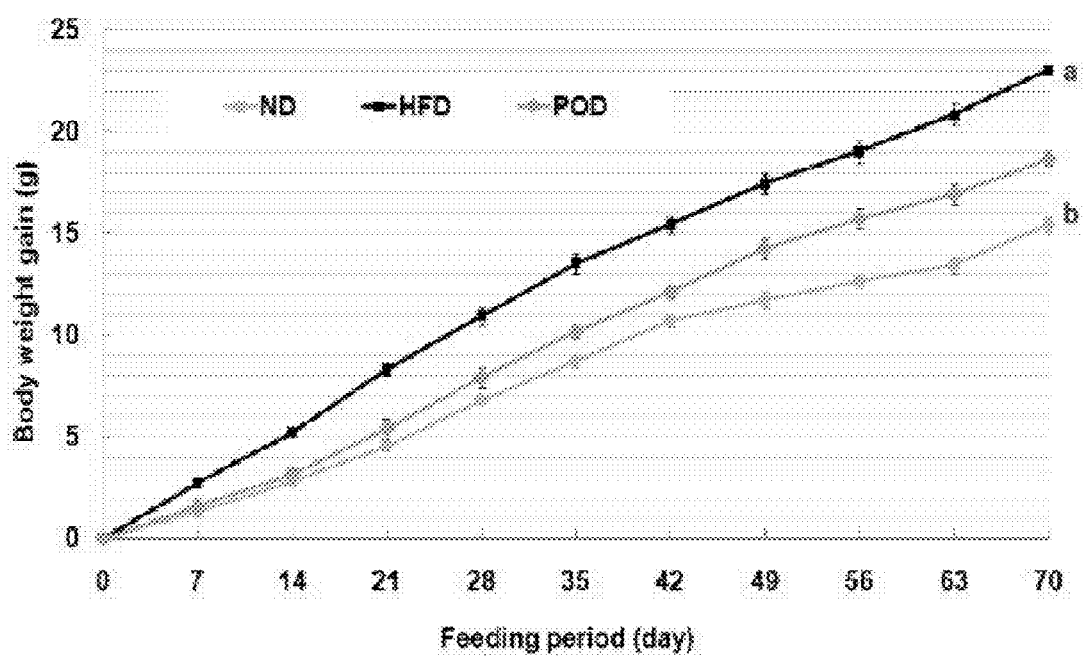
FIGS. 1a-1d represent body weight gain, daily food intake and feed efficiency of mice fed with test diets. The results are represented as mean±SEM (standard error) of values obtained from eight mice. The characters above the bars indicate significant difference among dietary groups by one-way analysis of variance (ANOVA) test and Duncan's multiple range test (P<0.001).
Figure 1B:
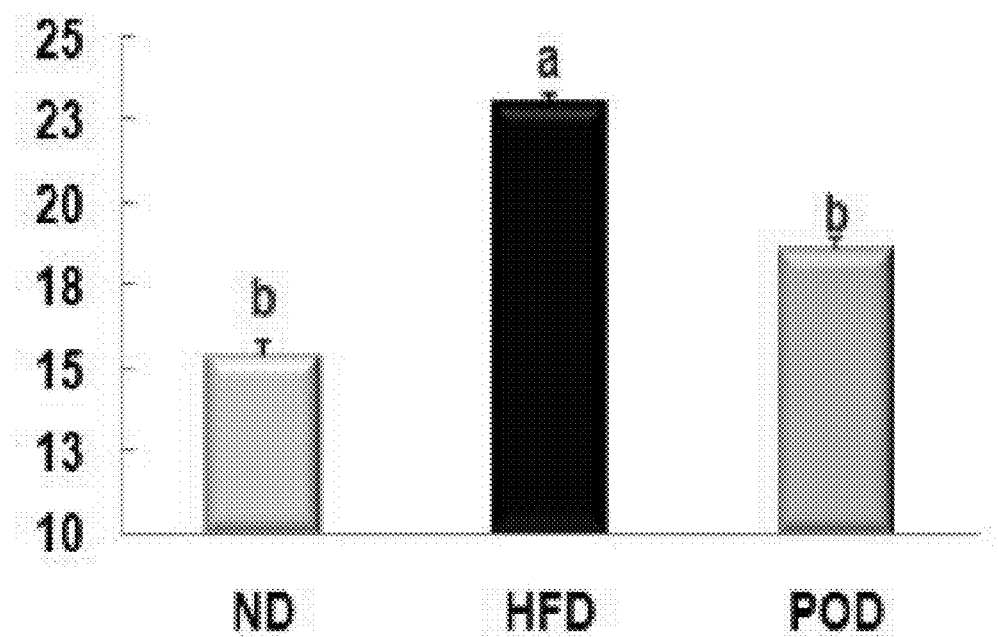
Figure 1C:
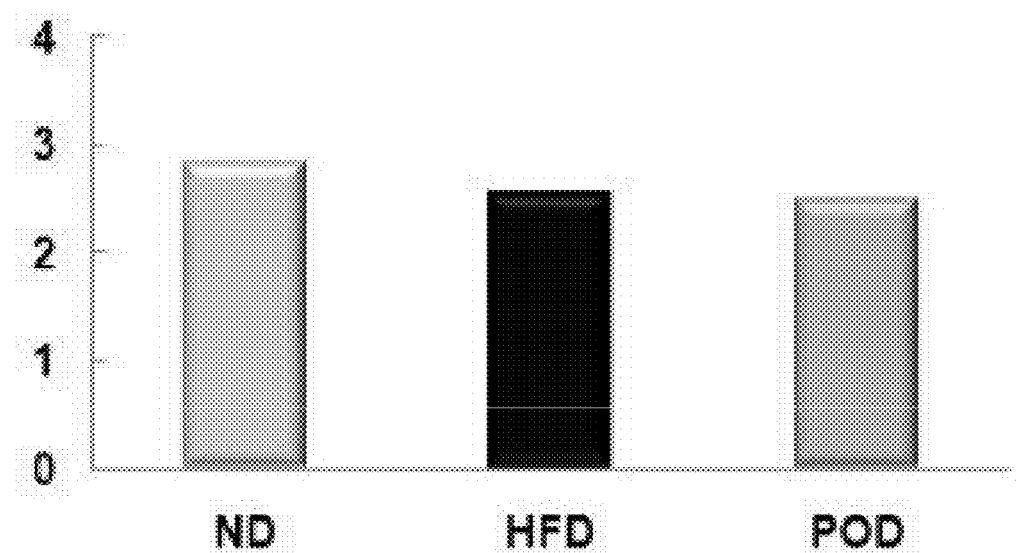
Figure 1D:
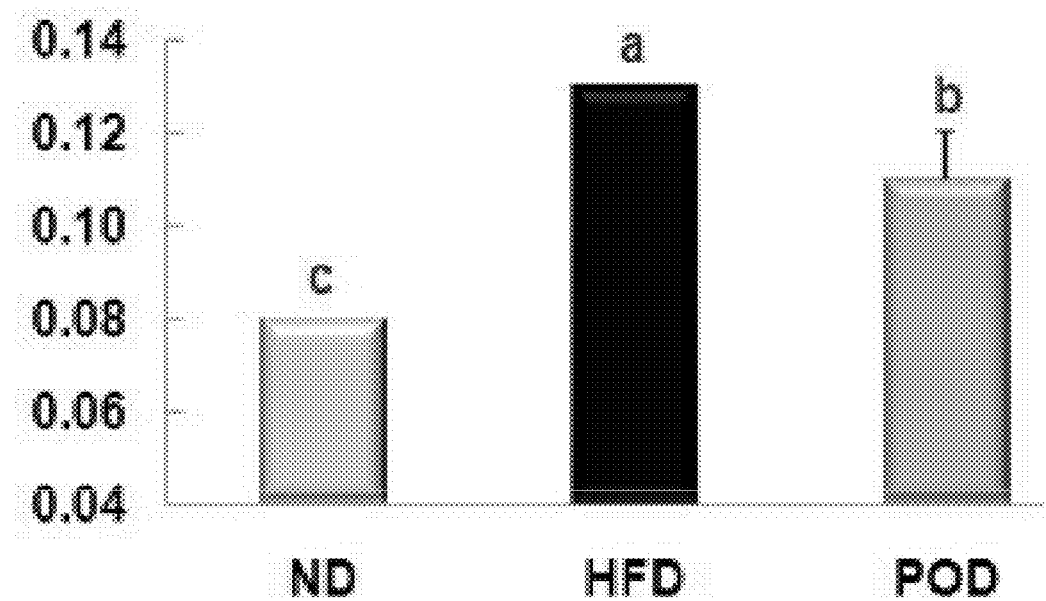

In one aspect of the present invention, there is provided a composition for preventing or treating metabolic diseases, comprising: piperonal as an active ingredient; wherein the metabolic disease is one or more selected from the group consisting of obesity, dyslipidemia, fatty liver and insulin resistance syndrome.

In another aspect of the present invention, there is provided a method for preventing or treating obesity, dyslipidemia, fatty liver and insulin resistance syndrome, comprising: administering to a subject in need thereof the composition comprising piperonal.

In still another aspect of the present invention, there is provided a method for preventing or improving obesity, dyslipidemia, fatty liver and insulin resistance syndrome, comprising: administering to a subject in need thereof the composition comprising piperonal.

The present inventors have made intensive studies to develop natural substance or compounds derived from natural substance having prevention or therapeutic efficacies for metabolic diseases including obesity, dyslipidemia and/or fatty liver. As a result, they have found out that piperonal is significantly effective in improvement of the lipid metabolic diseases.

According to the present invention, piperonal induces decreases in body weight, visceral fat, levels of plasma lipids such as triglyceride, total cholesterol, LDL+VLDL cholesterol, free fatty acid and triglyceride level of liver tissues, thereby considerably alleviating obesity induced by HFD (high-fat diet). Furthermore, the gene expressions of both nuclear transcription factors and their target gene which are increased by obesity induced with HFD, are decreased by piperonal administration and the gene expressions of TNF-α and IL-6 are also decreased significantly to attenuate inflammatory responses in progressive non-alcoholic fatty liver.

As used herein, the term "dyslipidemia" refers to hyperlipidemia, including abnormal lipid conditions caused by aberrant lipoprotein metabolism as well as hypercholesterolemia, hypertriglyceridemia and low HDL-cholesterolemia.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. As used herein, the term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or by insulin resistance.

As used herein, the term "insulin resistance" refers to a condition in which the natural hormone insulin becomes less effective at lowering blood sugars. When insulin resistance is high, the human body creates too much insulin to result in developments of not only hypertension and dyslipidemia but also heart diseases and diabetes. Especially, in type 2 diabetes, the increase in insulin is unrecognized in muscle and fat tissue, such that insulin action does not occur.

As used herein the term "insulin resistance syndrome" refers to a general term for disease which is induced by insulin resistance. It is characterized by cell resistance against insulin action, hyperinsulinemia, increase of very low density lipoprotein (VLDL) and triglyceride, decrease of high density lipoprotein (HDL) and hypertension. The insulin resistance syndrome is usually considered as a risk factor for cardiovascular disease and type 2 diabetes (Reaven G M, Diabetes, 37:1595-607 (1988)). In addition, it has been reported that insulin resistance increases intracellular oxidative stress together with risk factors such as hypertension, diabetes and smoking, and alters signal transduction to cause inflammatory responses, such that arteriosclerosis is developed (Freeman B A. Et al., Lab Invest. 47: 412-26, (1982)), Kawamura M. et al, J Clin Invest. 94: 771-8 (1994)).

As used herein the term "metabolic diseases" refer to a group of a wide variety of diseases caused by risk factors for various cardiovascular diseases and type 2 diabetes, including insulin resistance and its related diverse and complicated metabolic and clinical abnormalities. In 1988, Reaven suggested that a common cause of these symptoms is insulin resistance and named insulin resistance syndrome; however, in 1998, WHO newly introduced the term "metabolic syndrome or metabolic diseases", because insulin resistance may not explain all the elements of these symptoms.

The composition of the present invention comprising piperonal as an active ingredient has activity for improving diverse diseases of metabolic diseases such as obesity, dyslipemia, fatty liver or insulin resistance syndrome. The composition of the present invention may prevent or treat metabolic diseases by its various action mechanisms.

According to a preferred embodiment, the dyslipidemia of the present invention is a hyperlipidemia.

As used herein the term "hyperlipidemia" refers to a disease caused by higher level of blood lipids due to poor metabolism of lipids such as triglyceride and cholesterol. More specifically, hyperlipidemia is characterized by increased levels of lipids such as triglyceride, LDL cholesterol, phospholipids and free fatty acids in blood, including hypercholesterolemia and hypertriglyceridemia.

According to a preferred embodiment, the insulin resistance syndrome treated by the present invention comprises one or more selected from the group consisting of obesity, hypertension, arteriosclerosis, hyperlipidemia, hyperinsulinemia, non-alcoholic fatty liver disease and type 2 diabetes caused by insulin resistance.

According to a preferred embodiment, the composition of the present invention decreases levels of blood fat, liver fat or visceral fat.

As used herein the term "liver" or "visceral" is used to encompass organ, tissue and cell.

According to the present invention, the groups fed with the composition of the present invention showed significantly reduced lipid level in blood and liver tissues, and the total visceral fat weight was significantly reduced by 15% as compared to HFD.

According to a more preferred embodiment, the fat reduced by the present invention comprises triglyceride, cholesterol or free fatty acid.

According to a more preferred embodiment, the visceral fat reduced by the present invention comprises epididymal fat, perirenal fat, mesenteric fat and/or retroperitoneal fat.

According to the present invention, the groups fed with the composition of the present invention showed significantly reduced weights of the epididymal (by 11%), perirenal (by 35%), mesenteric fat-pad (by 20%), and retroperitoneal fat-pad (by 8%) as compared to HFD.

According to a preferred embodiment, the composition of the present invention decreases the level of ALT (alanine aminotransferase) or AST (aspartate aminotransferase) in blood.

As used herein the term "ALT (alanine aminotransferase)" and "AST (aspartate aminotransferase)" as indicators for liver function are enzymes exhibiting increased levels in blood upon damage of liver.

According to the present invention, the composition of the present invention significantly reduced both ALT (by 27%) and AST (by 15%) in the blood as compared to HFD-fed groups, addressing that piperonal has the excellent efficacies of improving fatty liver, preferably non-alcoholic fatty liver.

According to a preferred embodiment, the composition of the present invention decreases the expression of PPARγ (Peroxisome proliferator activated receptor gamma), C/EBPs (CCAAT enhancer-binding proterins) or aP2 (fatty acid binding protein).

The composition of the present invention decreases the expression of not only PPARγ and C/EBPs but also aP2 as their target gene, finally decreasing amount of visceral fat. The aP2 gene is expressed during preadipocyte proliferation and differentiation to adipocytes and its expression is regulated by PPARγ and C/EBPs.

According to a preferred embodiment, the composition of the present invention decreases the expression of TNF-α (tumor necrosis factor-alpha) and IL-6 (interleukin-6).

It has been reported that when obesity is induced by HFD, free fatty acids (especially saturated fat) in body fluids are increased. The free fatty acids as ligands bound to TLR4 activate IKK and then NF-κB, and stimulate the secretion of pro-inflammatory cytokines such as TNF-α and IL-6 to cause inflammatory response. In addition, TNF-α and IL-6 activate both the cytokine signaling 3 (SOCS3) and JNK and induce phosphorylation of serine residues of insulin receptor substrates (IRS) to inhibit glucose transport, finally causing insulin resistance in peripheral tissues of liver or muscle.

According to a preferred embodiment, the composition of the present invention increases the expression of UCP1 (uncoupling protein 1) or UCP3 (uncoupling protein 3).

As used herein the term "UCP1 (uncoupling protein 1)" and "UCP3 (uncoupling protein 3)" are mitochondrial proteins and found mainly in brown adipose tissue and skeletal muscles, respectively. These proteins lead to heat generation in mitochondria to increase cellular energy consumption, which act as excellent targets for anti-obesity drugs.

According to the present invention, the composition of the present invention increases the expression of UCP1 or UCP3 to promote thermogenesis, finally exhibiting anti-obesity effects.

According to a preferred embodiment, the composition of the present invention decreases the glucose level in blood.

According to the present invention, the composition of the present invention significantly reduced fasting blood sugar level (by 27%) to improve insulin resistance, thereby exhibiting prevention or treatment for metabolic diseases.

According to a preferred embodiment, piperonal of the present invention is derived from plants.

Piperonal used in the present invention may be extracted from plants. Preferably, it may be extracted or fractionated from plants such as *Capparis spinosa* Linne (Caper), *Cinnamomum camphora* (Camphor), *Cucumis melo* Linn, *Galium verum* var. *asiaticum*, *Piper nigrum* (Black Pepper), *Polianthes tuberosa* (Tuberose), *Vaccinium corymbosum* (American blueberry), *Vanilla planifolia* (Bourbon vanilla), *Viola odorata* (Apple leaf).

The plant extracts containing piperonal may be prepared using various extraction solvents. Preferably, the extraction solvent includes (a) absolute or hydrous lower alcohol containing 1-4 carbon atoms (e.g., methanol, ethanol, propanol, butanol, n-propanol, iso-propanol and n-butanol), (b) mixture of lower alcohol and water, (c) acetone, (d) ethyl acetate, (e) chloroform, (f) 1,3-butyleneglycol, (g) hexane, (h) diethylether, (i) butyl acetate or (j) water.

The plant fractions containing piperonal may be obtained by additional isolation/purification of the plant extracts to give further isolated/purified forms. For instance, it could be appreciated that active fractions obtained using a variety of additional purification methods such as an ultrafiltration with defined molecular weight cut-off value and various chromatography (designed for purification dependent upon size, charge, hydrophobicity and affinity) are included in the present plant fractions. Alternatively, piperonal may be chemically synthesized in a mass production manner.

According to a preferred embodiment, the composition of the present invention is a pharmaceutical composition for preventing or treating obesity, dyslipidemia, fatty liver or insulin resistance syndrome.

When the composition of the present disclosure is prepared as a pharmaceutical composition, the pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in Remington's Pharmaceutical Sciences (19th ed., 1995).

The pharmaceutical composition of the present disclosure may be administered orally or parenterally. Preferably, it may be administered orally.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

According to a preferred embodiment, the composition of the present invention is a food composition for preventing or improving obesity, dyslipidemia, fatty liver or insulin resistance syndrome.

When the composition of the present disclosure is prepared as a food composition, the food composition of the present disclosure may comprise, in addition to piperonal of the present disclosure as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.)] or a synthetic flavor (saccharin, aspartame, etc.).

For example, when the food composition of the present disclosure is prepared as a drink, it may further comprise, in addition to piperonal of the present disclosure as the active ingredient, citric acid, high-fructose corn syrup, sugar, glucose, acetic acid, malic acid, fruit juice, eucommia extract, jujube extract, licorice extract, or the like.

The features and advantages of the present invention may be summarized as follows:

(a) The present composition containing piperonal as an active ingredient is very effective in preventing or treating obesity, dyslipidemia, fatty liver or insulin resistance syndrome (preferably, dyslipidemia or fatty liver, more preferably hyperlipidemia or fatty liver).

(b) Piperonal as active ingredients for the present composition may be isolated from various plants and chemically synthesized.

(c) The composition of the present invention useful as pharmaceuticals compositions or functional food compositions has therapeutic efficacies for obesity, hyperlipidemia or fatty liver, and also induces significant decrease in fasting glucose level and blood insulin level to improve type 2 diabetes, insulin resistance and related metabolic disorders.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Reduction of Body and Visceral Fat-Pad Weights by Piperonal

1) Preparation of Test Diets and Maintenance of Test Animals

The obesity-inducing control diet used in the test was high-fat diet (HFD: 40% fat calorie, 17 g lard+3% corn oil/100 g diet). Diets supplemented with piperonal (piperonal-supplemented high fat diet, POD) had the same composition as HFD, except that piperonal was included at 0.05%. The normal diet (ND) was prepared under AIN-76 rodent diet (American Institute of Nutrition, Report of the American Institute of Nutrition ad hoc committee on standards for nutritional studies. J. Nutr. 107: 1340-1348, 1977) (see Table 1). Piperonal was purchased from Sigma-Aldrich.

TABLE 1

Compositions of test diets

| Ingredients | Normal diet (HFD) (g/kg diet) | High-fat diet (HFD) (g/kg diet) | Piperonal-supplemented diet (POD) (g/kg diet) |
| --- | --- | --- | --- |
| Casein | 200 | 200 | 200 |
| D/L-Methionine | 3 | 3 | 3 |
| Corn starch | 150 | 111 | 110.5 |
| Sucrose | 500 | 370 | 370 |
| Cellulose | 50 | 50 | 50 |
| Corn oil | 50 | 30 | 30 |
| Lard | — | 170 | 170 |
| Vitamin complex | 10 | 12 | 12 |
| Mineral complex | 35 | 42 | 42 |
| Choline bitartrate | 2 | 2 | 2 |
| Cholesterol | — | 10 | 10 |
| Tert-butylhydroquinone | 0.01 | 0.04 | 0.04 |
| piperonal | — | — | 0.5 |
| Total (g) | 1,000 | 1,000 | 1000 |
| Fat (% calorie) | 11.5 | 39.0 | 39.0 |
| Total calorie (kJ/kg diet) | 16,439 | 19,315 | 19,315 |

5-week-old male C57BL/6J mice (Orient, Korea) were accustomed to the laboratory environment for 1 week while feeding solid feed. Then, they were randomly divided into normal diet, high-fat diet and test groups and bred for a total of 10 weeks. The diet was given between 10 and 11 a.m. every day together with water. Food intake was measured every day and body weight was measured once a week. In order to avoid transient body weight increase after feed intake, body weight was measured 2 hours after removing the feed. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes for the separation of plasma.

2) Changes of Body and Visceral Fat-Pad Weights

Figure 2:
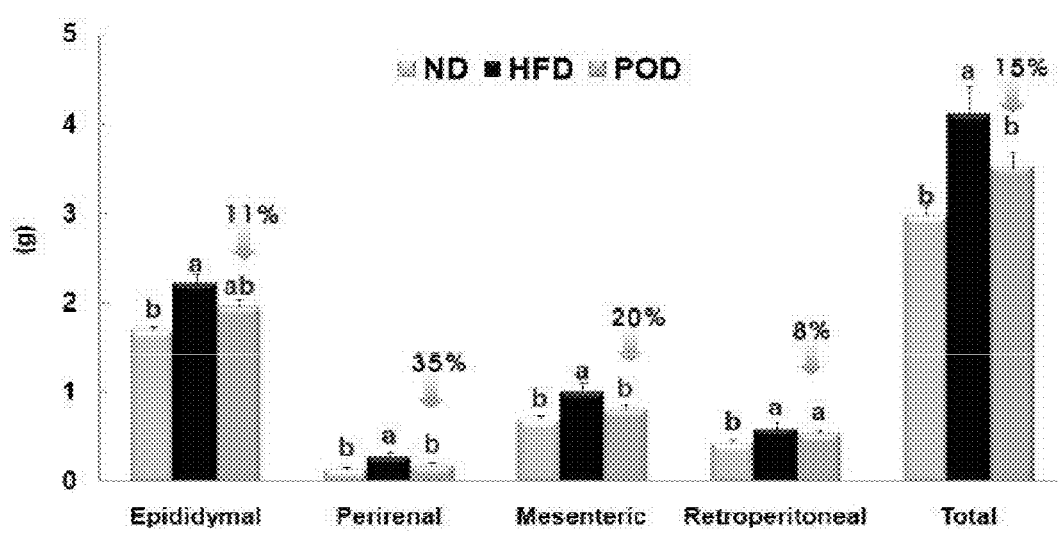
FIG. 2 shows visceral fat-pad weight (g) of mice fed with test diets. The results are represented as mean±SEM (standard error) of values obtained from eight mice. The characters above the bars indicate significant difference among dietary groups by one-way analysis of variance (ANOVA) test and Duncan's multiple range test (P<0.001).

After feeding the test diet for 10 weeks, the piperonal-supplemented group showed significant decrease of body weight gain by 19% as compared to HFD. The dietary supplementation with piperonal induced no significant change in the daily food intake, and reduced significantly the food efficiency ratio by 15% as compared to HFD. The food efficiency ratio was calculated by dividing the total body weight gain during the experimental period (g) by the total food intake (g) (FIGS. 1 and 2). Therefore, it would be understood that the body weight-decreasing effect by piperonal is not due to the suppression of appetite.

Figure 3:
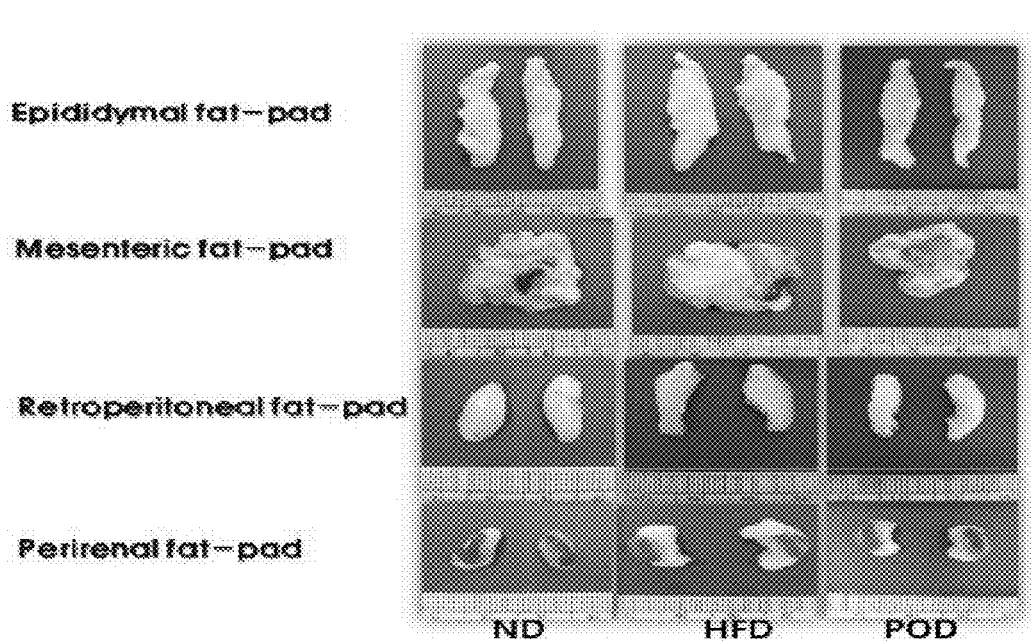
FIG. 3 represents images of visceral fat tissues of mice fed with test diets.
Figure 4:
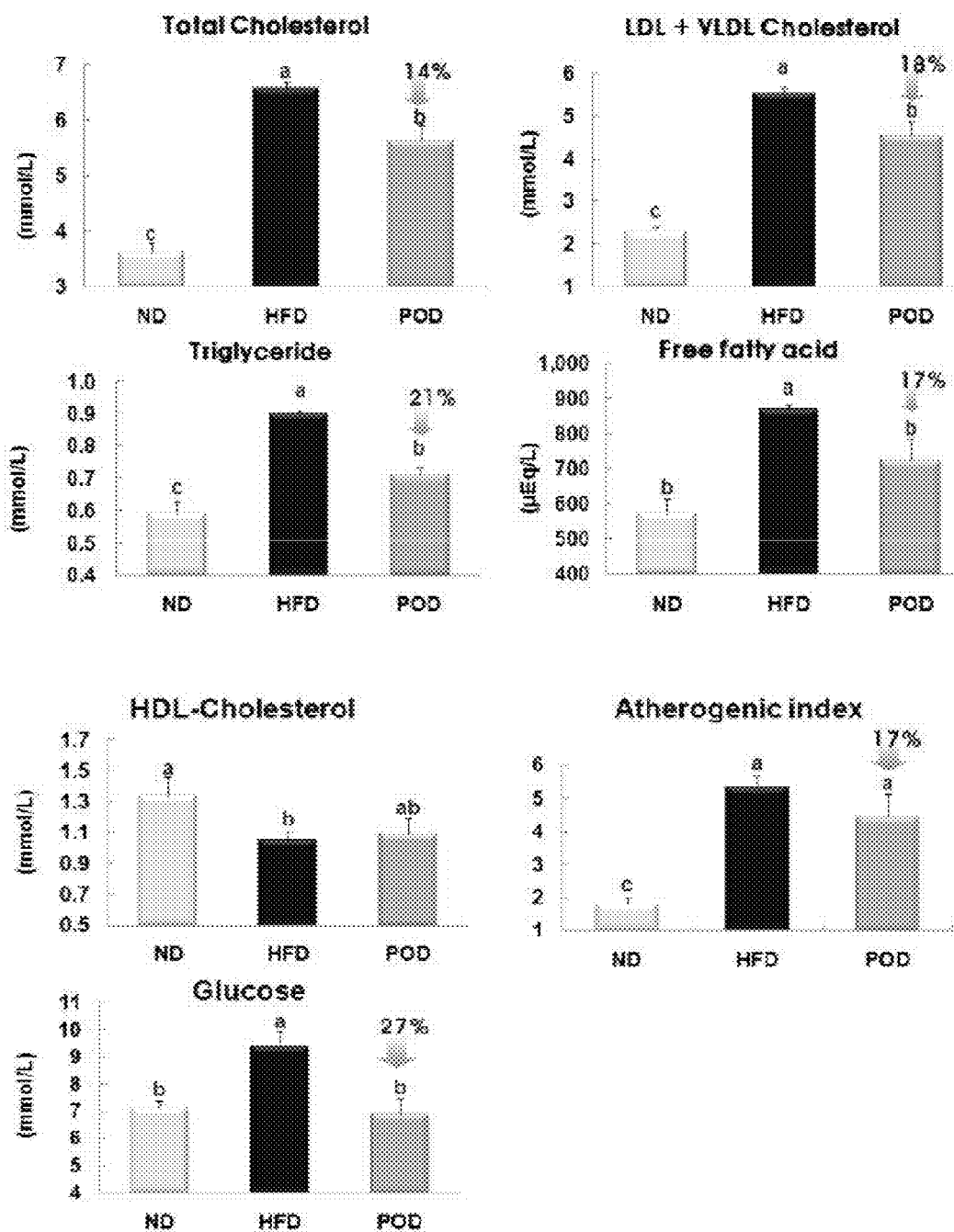
FIG. 4 shows plasma levels of lipid and glucose in mice fed with piperonal. The results are represented as mean±SEM (standard error) of values obtained from eight mice. The characters above the bars indicate significant difference among dietary groups by one-way analysis of variance (ANOVA) test and Duncan's multiple range test (P<0.05).

After feeding the test diet for 10 weeks, the epididymal, perirenal, mesenteric, and retroperitoneal fat-pads contained in the visceral fat were removed and weighed. The piperonal-supplemented group showed significantly reduced weights of the epididymal (by 11%), perirenal (by 35%), mesenteric fat-pad (by 20%), and retroperitoneal fat-pad (by 8%) as compared to HFD. The total visceral fat weight was significantly reduced by 15% in the POD group than in the HFD group (P<0.001) (FIGS. 3 and 4). Accordingly, it would be appreciated that piperonal has excellent effects to reduce body weights and visceral fat-pad weights.

Example 2: Prevention and Treatment of Hyperlipidemia and Type 2 Diabetes by Piperonal 1) Biochemical Analysis of Blood After 10 weeks of breeding, total cholesterol, HDL-cholesterol, triglyceride and glucose levels in the plasma and lipid levels in the liver tissue were measured as follows. Total cholesterol, HDL-cholesterol, triglyceride, free fatty acid and glucose levels in the plasma were measured twice for each using a commercially available kit (Bio Clinical System). LDL+VLDL cholesterol levels in the blood were calculated by subtracting HDL-cholesterol levels from the total cholesterol levels.

2) Changes of Plasma Lipid and Glucose Levels

Figure 5:
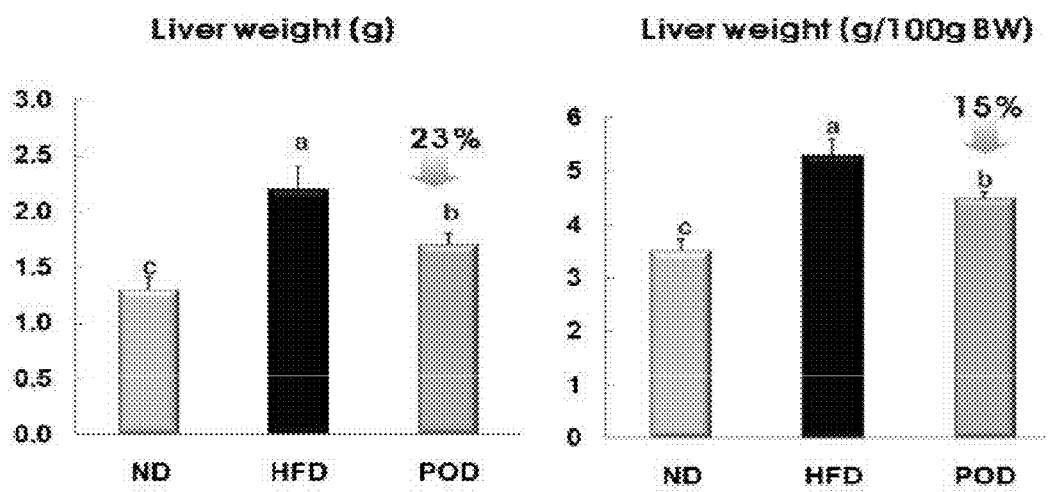
FIG. 5 represents liver weights of mice fed with piperonal. The results are represented as mean±SEM (standard error) of values obtained from eight mice. The characters above the bars indicate significant difference in dietary groups by one-way analysis of variance (ANOVA) test and Duncan's multiple range test (P<0.001).

After feeding the test diet for 10 weeks, the piperonal-supplemented group showed significantly lower plasma levels of triglyceride (by 21%), total cholesterol (by 14%), LDL+VLDL cholesterol (by 18%), free fatty acid (by 17%) and atherogenic indices (by 17%) as compared to the HFD group (FIG. 5). Moreover, piperonal supplemented to the HFD resulted in a significant reduction of the fasting blood sugar level by 27%, as compared to HFD. Accordingly, it could be recognized that piperonal has the excellent effects of improving hyperlipidemia and fasting blood sugar level in obesity induced by the HFD.

Example 3: Prevention and Treatment of Non-Alcoholic Fatty Liver by Piperonal 1) Analysis of Lipid Level in Liver Tissues Lipids were extracted from the liver tissue according to Folch et al.'s method (Folch J et al., J Biol Chem. 226:

497-509 (1957)). After adding 1 mL of distilled water to 0.25 g of liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed.

The same kit (Bio Clinical System) as that used for the plasma analysis was used to measure the triglyceride, cholesterol and free fatty acid levels of the liver tissue.

The activity of ALT (alanine aminotransferase) and AST (aspartate aminotransferase) used as liver function indicator were measured twice for each using a commercially available kit (Bio Clinical System, Korea).

2) Changes of Liver Weights and Liver Lipid Levels and Liver Function Indicator

Figure 6:
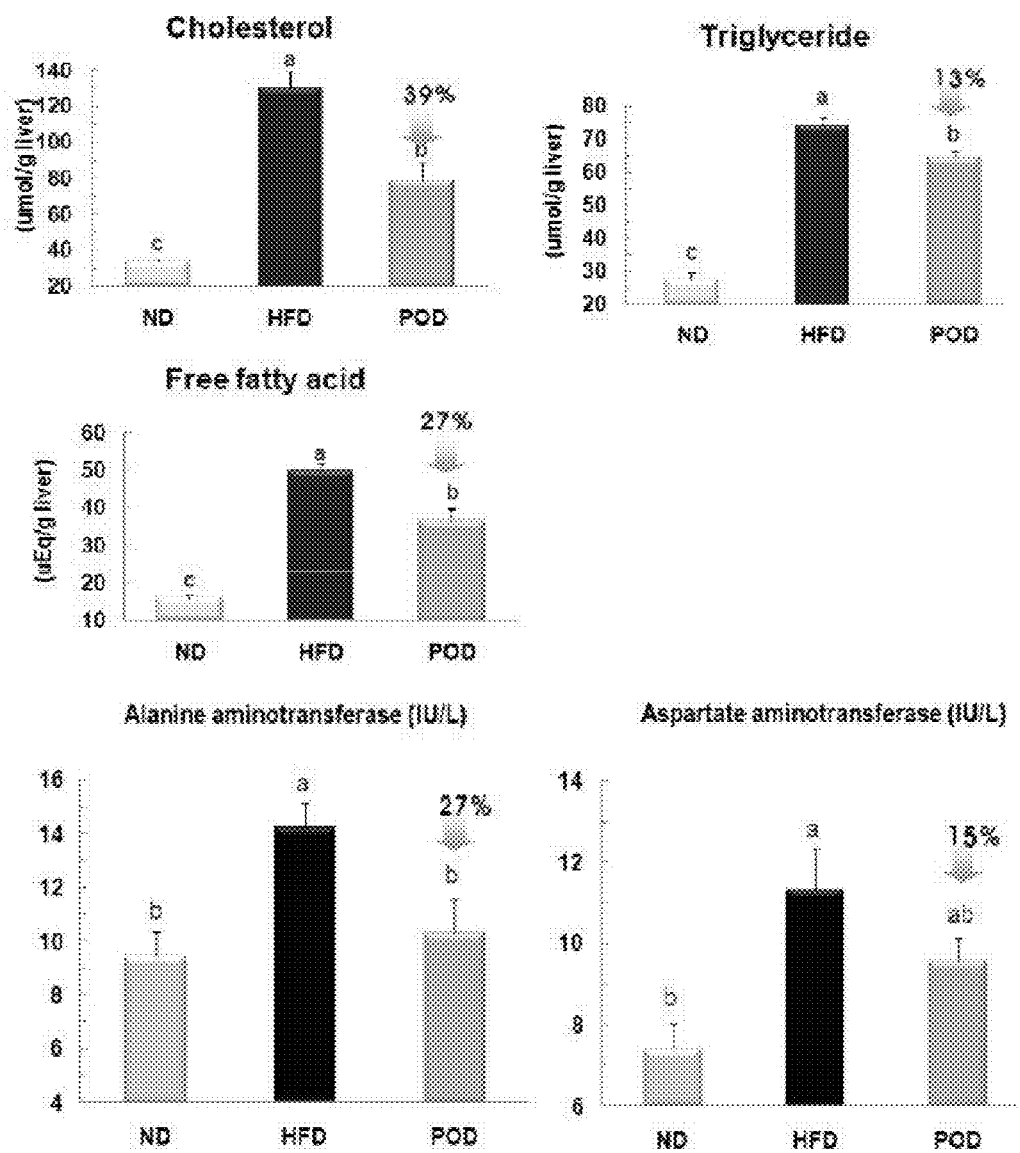
FIG. 6 shows hepatic lipid levels and hepatic function parameters in mice fed with piperonal. The results are represented as mean±SEM (standard error) of values obtained from eight mice. The characters above the bars indicate significant difference among dietary groups by one-way analysis of variance (ANOVA) test and Duncan's multiple range test (P<0.05).
Figure 7:
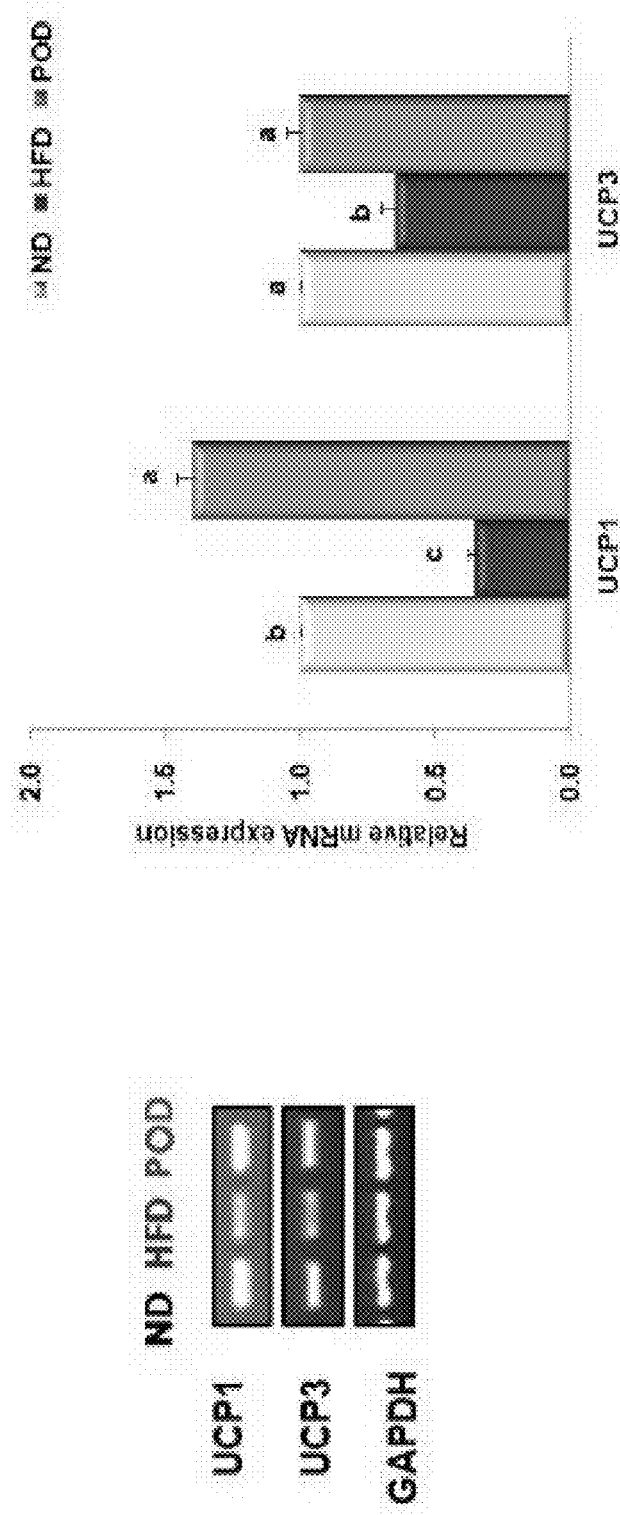
FIG. 7 represents the expression profiles of UCPs genes in the visceral fat tissues of mice. The left panel represents images of RT-PCR analysis results for UCP1 and UCP3, and the right panel represents relative expression levels of these genes. The data were normalized to GAPDH mRNA levels and expressed as relative values to those from ND mouse. The results are represented as mean±SEM (standard error) of values obtained from RNA sample of eight mice with three independent experiments. The characters above the bars indicate significant difference in dietary groups by one-way analysis of variance (ANOVA) test and Duncan's multiple range test (P<0.05).
Figure 8:
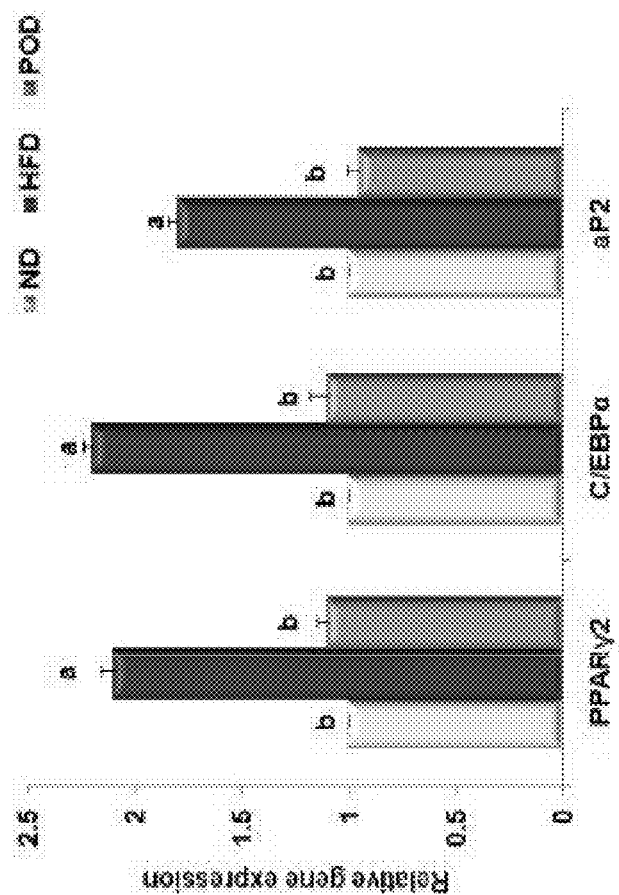
FIG. 8 represents the expression profiles of genes relating to lipogenesis in mice liver tissues. The left panel represents images of RT-PCR analysis results for C/EBPα, PPARγ2 and aP2, and the right panel represents relative expression levels of these genes. The data were normalized to GAPDH mRNA levels and expressed as relative values to those from ND mouse. The results are represented as mean±SEM (standard error) of values obtained from RNA sample of eight mice with three independent experiments. The characters above the bars indicate significant difference in dietary groups by one-way analysis of variance (ANOVA) test and Duncan's multiple range test (P<0.05).
Figure 8:
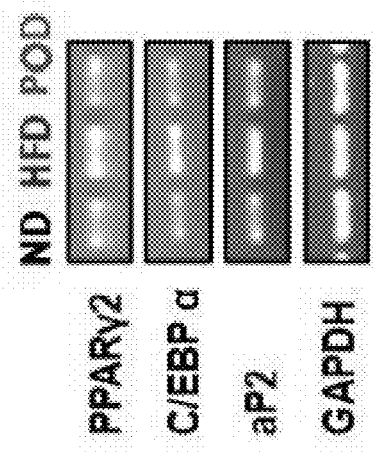
Figure 9:
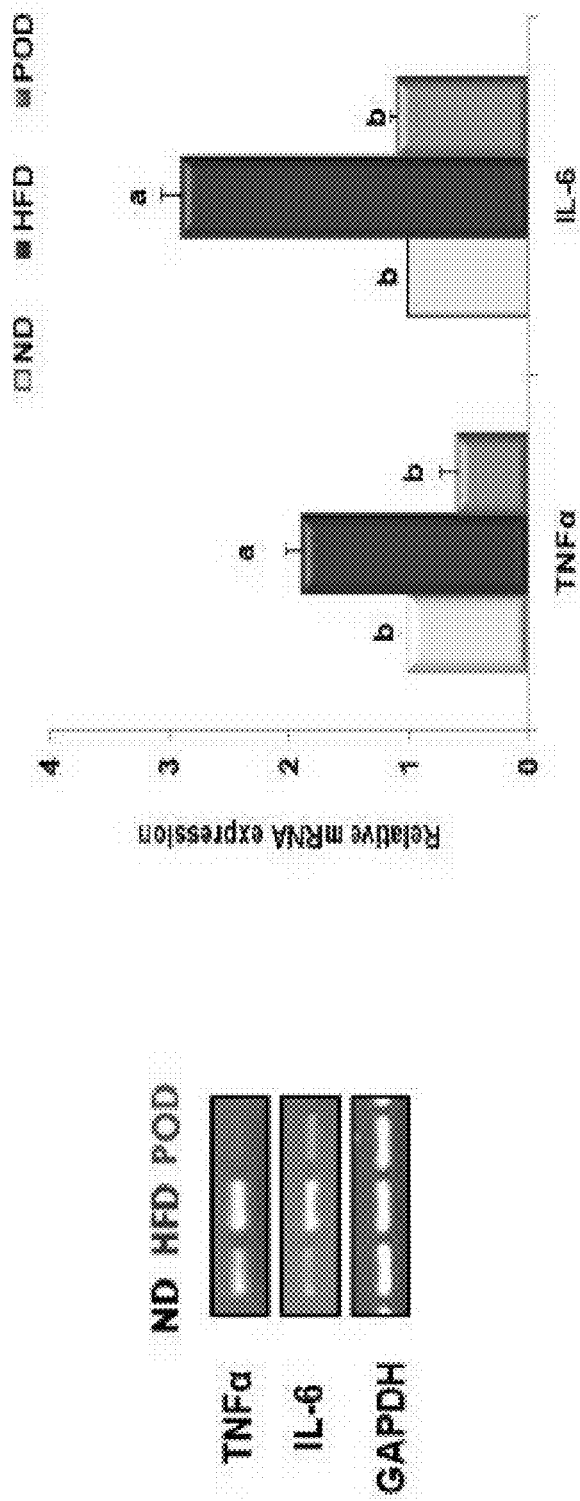
FIG. 9 represents the expression profiles of genes relating to inflammation in mice liver tissues. The left panel represents images of RT-PCR analysis results for TNFα and IL-6, and the right panel represents relative expression levels of these genes. The data were normalized to GAPDH mRNA levels and expressed as relative values to those from ND mouse. The results are represented as mean±SEM (standard error) of values obtained from RNA sample of eight mice with three independent experiments. The characters above the bars indicate significant difference in dietary groups by one-way analysis of variance (ANOVA) test and Duncan's multiple range test (P<0.05).

After feeding the test diet for 10 weeks, the piperonal-supplemented group showed significantly decreased levels of absolute organ weights (by 23%) and relative organ weights (g/100 g body weight) (by 15%) in liver tissue as compared to HFD (FIG. 6). The piperonal-supplemented group showed significantly decreased levels of triglyceride (by 13%), cholesterol (by 39%) and free fatty acid (by 27%) in liver tissue as compared to HFD. Moreover, the HFD group exhibited significantly higher plasma activities of ALT (alanine aminotransferase) and AST (aspartate aminotransferase), which are parameters for hepatic function, as compared to the normal diet group and the POD group showed significantly decreased plasma activities of ALT (by 27%) and AST (by 15%) as compared to the HFD group (FIG. 7). Accordingly, it could be understood that piperonal has the excellent effect of significantly improving fatty liver in obesity induced by HFD.

Example 4: Inhibitory Effects of UCP (Uncoupling Protein) Gene Expressions in Mouse Visceral Fat Tissues by Piperonal 1) RNA Extraction and RT-PCR (Reverse Transcription-Polymerase Chain Reaction) Analysis After adding 1 mL of Trizol agent per 0.1 g of visceral fat tissues, the mixture was homogenized and centrifuged at 12,000×g for 10 min at 4° C. The supernatant was transferred to a new tube and 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

The RNA sample obtained from the visceral fat tissues was transcribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 2. The amplified products 1 μl were resolved on agarose gel electrophoresis to identify DNA band.

TABLE 2

Primer sequences for RT-PCR

| Gene | Primer | Sequence(5'→3') | Anealing Temp (° C.) | Size of PCR product (bp) |
| --- | --- | --- | --- | --- |
| Uncouplin protein 1 (UCP1) | forward primer reverse primer | GGGACCTACAATGCTTACAG GGTCATATGTCACCAGCTCT | 55 | 103 |
| Uncouplin protein 3 (UCP3) | forward primer reverse primer | ACGGATGTGGTGAAGGTCCG TACAAACATCATCACGTTCC | 55 | 464 |
| Glyceraldehyde-3-phosphate-dehydrogenase (GAPDH) | forward primer reverse primer | AGAACATCATCCCTGCATCC TCCACCACCCTGTTGCTGTA | 55 | 321 |

2) Results of RT-PCR Analysis of Visceral Fat Tissues

The dysfunction of mitochondria is related to senescence, heart diseases and gastrointestinal, endocrine and neurological disorders. The damages of the oxidation process in mitochondria increase glucose production in liver tissues and hyperglycemia, finally causing fatty liver. The mitochondria forms proton gradient across its inner and outer membranes by the electron transport chain, and generates ATP through F0F1-ATPase using the proton gradient as a driving force. Where F0F1-ATPase is not normally worked, the proton gradient disappears through uncoupling proteins to generate heat. In current, it has been reported that UCPs in adipose tissues promotes thermogenesis with maintaining redox balance by the energy-dissipatory mechanism. Therefore, UCPs as well as AMPK (AMP-activated protein kinase) become highlighted as novel targets for obesity treatment.

After extracting mRNA from the visceral fat tissues of mice fed test diet, RT-PCR analysis was performed. As a result of measuring the expression levels of UCP1 and UCP3 regulating thermogenesis in body, the expressions of UCP1 and UCP3 genes were significantly decreased in the HFD group compared with the ND group. In contrast, these HFD-induced decrease in expressions of UCP1 and UCP3 were significantly reversed by feeding piperonal to the similar level to the ND group. Therefore, it would be understood that piperonal significantly improves obesity-caused inhibition of thermogenesis in visceral fat tissues.

Example 5: Changes of Gene Expressions in Mouse Liver Tissues by Piperonal

1) RNA Extraction and RT-PCR (Reverse Transcription-Polymerase Chain Reaction) Analysis After adding 1 mL of Trizol agent per 0.1 g of liver tissues, the mixture was homogenized and centrifuged at 12,000×g for 10 min at 4° C. The supernatant was transferred to a new tube and 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

The RNA sample obtained from the liver tissues was transcribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 3. The amplified products 1 μl were resolved on agarose gel electrophoresis to identify DNA band.

2) Results of RT-PCR Analysis in Mouse Liver Tissues

In process of generating non-alcoholic fatty liver, lipids are accumulated and adipocyte-specific genes such as aP2 (fatty acid binding protein), LPL (lipoprotein lipase) and adipsin are expressed under controls of three transcription factors including PPARγ (Peroxisome proliferator activated receptor gamma), C/EBPs (CCAAT enhancer-binding proterins) and SREBP-1c (sterol regulatory binding protein-1c) which play an important role.

The mRNA expressions of liver tissues were evaluated by RT-PCR analysis. The HFD group showed significantly increased expressions of C/EBPα, PPARγ2 and aP2 genes as compared to the ND. Nuclear transcription factors, C/EBPα and PPARγ2, play an important role in adipogenesis and aP2 is the target gene for these transcription factors. In contrast, piperonal supplemented to the HFD significantly decreased the expression of C/EBPα, PPARγ2 and aP2 genes to levels similar for the ND. Accordingly, it could be understood that piperonal prevented generation of fatty liver by decreasing the expression of nuclear transcription factors and their target gene.

The mRNA expression profiles of pro-inflammatory cytokines in liver tissues were evaluated using RT-PCR. The HFD group exhibited significantly higher levels of both TNF-α and IL-6 gene expressions as compared to the ND. Meanwhile, these HFD-induced elevations in the expression of TNF-α and IL-6 were significantly reversed by feeding piperonal. Accordingly, it would be concluded that piperonal has the excellent effects of improving inflammatory responses in progressive non-alcoholic fatty liver.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

TABLE 2

Primer sequences for RT-PCR

| Gene | Primer | Sequence(5'→3') | Anealing Temp (° C.) | Size of PCR product (bp) |
|---|---|---|---|---|
| PPARγ2 (Peroxisome proliferator activated receptor gamma) | forward primer reverse primer | TTCGGAATCAGCTCTGTGGA CCATTGGGTCAGCTCTTGTG | 55 | 148 |
| aP2 (Fatty acid binding protein) | forward primer reverse primer | AGCATCATAACCCTAGATGG GAAGTCACGCCTTTCATAAC | 55 | 128 |
| C/EBPα (CCAAT/enhancer binding protein alpha) | forward primer reverse primer | TCGGTGCGTCTAAGATGAGG TCAAGGCACATTTTTGCTCC | 55 | 187 |
| TNFα | forward primer reverse primer | TGTCTCAGCCTCTTCTCATT AGATGATCTGAGTGTGAGGG | 55 | 156 |
| IL-6 (Intereukin 6) | forward primer reverse primer | ATGAAGTTCCTCTCTGCAAGAGACT CACTAGGTTTGCCGAGTAGATCTC | 55 | 638 |

What is claimed is:

1. A method for treating a subject having dyslipidemia, or lowering fasting glucose levels, comprising: administering to a subject in need thereof a composition consisting essentially of piperonal in purified form as the sole active ingredient, wherein the treatment results in an improvement in dyslipidemia, or lowering fasting glucose levels in the subject.

2. The method according to claim 1, wherein the dyslipidemia is hyperlipidemia.

3. The method according to claim 1, wherein the composition decreases the fasting glucose level in blood.

4. The method according to claim 1, the purified form of wherein piperonal is derived from a plant.

5. The method according to claim 1, wherein the composition is a pharmaceutical composition.

6. The method according to claim 1, wherein the composition is a food composition.

7. The method of claim 1, wherein the method is carried out to improve or treat dyslipidemia in a subject in need of such treatment.

8. The method of claim 1, wherein the method is carried out to lowering fasting glucose levels in a subject in need of such treatment.

9. The method of claim 1, wherein the composition consists of piperonal as the sole active ingredient and one or more pharmaceutically acceptable carriers or excipients.

10. The method of claim 1, wherein the composition consists of piperonal as the sole active ingredient and one or more components of a food or a drink.

* * * * *